United States Patent
Haskell et al.

(10) Patent No.: US 8,296,299 B2
(45) Date of Patent: Oct. 23, 2012

(54) GEOGRAPHY BRICKS FOR DE-IDENTIFICATION OF HEALTHCARE DATA

(75) Inventors: Tom Haskell, Havertown, PA (US); Karrie Hontz, Collegeville, PA (US)

(73) Assignee: IMS Software Services Ltd., Wilmington, DE (US)

( * ) Notice: Subject to any disclaimer, the term of this patent is extended or adjusted under 35 U.S.C. 154(b) by 305 days.

(21) Appl. No.: 12/621,476

(22) Filed: Nov. 18, 2009

(65) Prior Publication Data

US 2011/0040797 A1    Feb. 17, 2011

Related U.S. Application Data

(60) Provisional application No. 61/234,531, filed on Aug. 17, 2009.

(51) Int. Cl.
    *G06F 17/30*    (2006.01)

(52) U.S. Cl. ...................................................... 707/736
(58) Field of Classification Search ................. 707/2, 5, 707/736; 345/442
    See application file for complete search history.

(56) References Cited

U.S. PATENT DOCUMENTS 5,408,598 A * 4/1995 Pryor, Jr. ...................... 345/442
2009/0055382 A1 * 2/2009 Kerschbaum ..................... 707/5

* cited by examiner

*Primary Examiner* — Etienne Leroux
(74) *Attorney, Agent, or Firm* — Fish & Richardson P.C.

(57) ABSTRACT

Techniques of the described subject matter employ a break down algorithm in which a population of individuals is broken down into segments that have a greater number of individuals than a threshold minimum. Information on aggregated individuals may then be used to accomplish a variety of tasks, such as consumer purchasing preferences, market data analysis, sales force allocation, etc., without revealing the specific identity of any individuals or permitting others to determine, from the data, the identity of any individuals.

23 Claims, 8 Drawing Sheets

N-Tree Diagram

N-Tree Diagram

GEOGRAPHY BRICKS FOR DE-IDENTIFICATION OF HEALTHCARE DATA

CROSS-REFERENCE TO RELATED APPLICATION

The present application claims the benefit of U.S. Provisional Application No. 61/234,531, filed Aug. 17, 2009, which is incorporated by reference in its entirety herein.

BACKGROUND

Commercial organizations often use personally identified information for a variety of tasks, such as tracking customer purchase patterns, evaluating response to promotions, etc. The identification information can include highly confidential and/or personal information such as credit card numbers, customer numbers, employer names, addresses, email addresses, purchasing histories, web browsing histories, airline flight histories, and the like. In the healthcare industry, sensitive information can include health plan claims, physician identifiers, outcomes research, etc.

There has been increasing attention to responsible handling and use of such sensitive information, particularly in the healthcare industry, and industry participants, as well as Federal, State and local governments are implementing sensitive data regulations that can limit the use of personally identifying information. For example, some regulations may promote the responsible use and disclosure of data including such personally identifying information. Other regulations may permit the use of such information when the information is partially or completely de-identified (e.g., aggregated information where the granularity of the aggregation group size is above a selected threshold determined to preserve the secrecy of the sensitive information).

SUMMARY

The described subject matter provides for a modified N-Tree approach to group potential professionals into the smallest practical geographic boundaries required by specific business rule criteria.

In one exemplary embodiment, the disclosed subject matter provides a technique which starts at a state level and breaks down the state into continuously smaller geographic regions until each region cannot be broken down any further while preserving the required criteria for grouping. One such criteria for grouping is that the number of individuals in the region is no less than a threshold minimum. One end result is that areas with high densities of the professionals in question will be broken down into very small regions (sub-ZIP code), while professionals in less dense areas will be grouped in a larger region. Once the professionals are grouped, aggregate information about these professionals can be published without risking identification.

Some embodiments include techniques of de-identification of health care data, including segmenting, by a computer processor, a population region into at least one region, wherein a number of individuals within each region of the at least one region is greater than or equal to a preselected minimum threshold and aggregating data for the individuals within each region into data for the whole region. Each of the at least one regions can be the smallest possible region. Segmenting can include performing a recursive N-Tree break down procedure. The techniques can also include, at each level of the recursive segmentation procedure, breaking down a region into polygon shaped regions. The polygons can be rectangles, trapezoids, rhombi, triangles, and hexagons. The polygons can be of varying shapes. Other embodiments can include resegmenting one or more of the at least one regions to account for the migration of individuals from one region to another.

Some embodiments include techniques for receiving an indication of a minimum threshold number of individuals, wherein aggregating data for the individuals into data for the minimum threshold number of individuals is determined to preserve the secrecy of the sensitive healthcare data, segmenting, by a computer processor, a population region into at least one region, wherein a number of individuals within each region of the at least one region is greater than or equal to the minimum threshold, and storing boundaries for the at least one region.

DETAILED DESCRIPTION

Generally, techniques of the described subject matter employ a break down algorithm in which a population of individuals is broken down into segments that have a greater number of individuals than a threshold minimum. Information on aggregated individuals may then be used to accomplish a variety of tasks, such as market data analysis, sales force allocation, etc., without revealing the specific identity of any individuals or permitting others to determine, from the data, the identity of any individuals.

The sensitive nature of collection and use of health care information makes clear the need for techniques to both (i) protect the sensitive information of individual patients and (ii) preserve the confidentiality of the information. Country-specific data protection laws have been in place for many years, including the EU data protection directive, and the HIPAA regulations.

Certain federal, state, and local laws restrict the use of identified data in the healthcare arena, beyond the patient privacy regulations noted above. Use of information relating to physicians in their professional capacity may be considered sensitive and the use of that information restricted. The described subject matter will provide a mechanism to assure compliance with these regulations when viewing information related to physicians' professional practices. Examples include prescription data, health claims information, and diagnosis and treatment records. Of course, techniques of the presently described subject matter are applicable to areas other than healthcare, such as governmental agency data, retail customer data, financial data, and the like.

Figure 6:
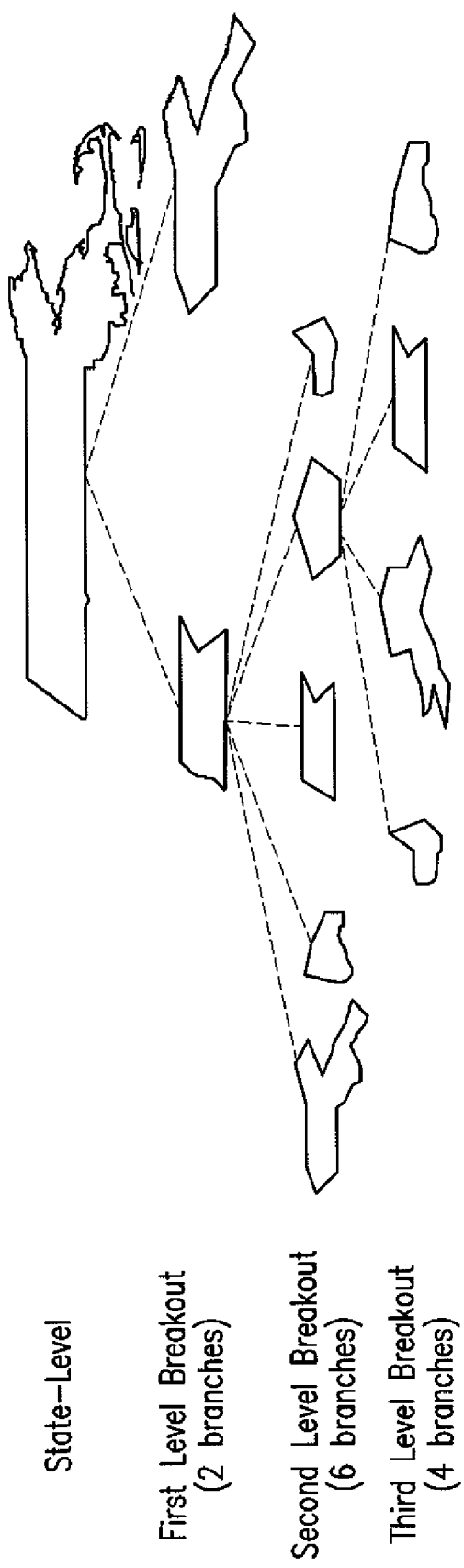
FIG. 6 illustrates another example break down according to techniques of the described subject matter.

The described techniques may include an N-Tree, recursive algorithm for breaking down the population into smaller and smaller segments until a segment cannot be broken down any further. The segments may be referred to as bricks or regions. It should be noted that bricks can include break down shapes other than rectangles, such as hexagons, triangles, shapes including curves, etc. The technique may be called an N-Tree technique because the recursive break-down of the state creates a tree-like structure with branches. "N" may used to specify that there can be any number of branches per break-down. FIG. 6 illustrates an example of a break-down where the first level is broken down into 2 branches. The left-most branch is then broken down into 5 more branches, etc.

In some embodiments, the N-Tree approach may include techniques for addressing updates to the geographic regions when individuals move in and out of the segments. To avoid re-categorization of each individual by re-calculating the complete N-Tree, for updates, in some embodiments, re-calculation is limited to the affected branches of the N-Tree.

Figure 7:
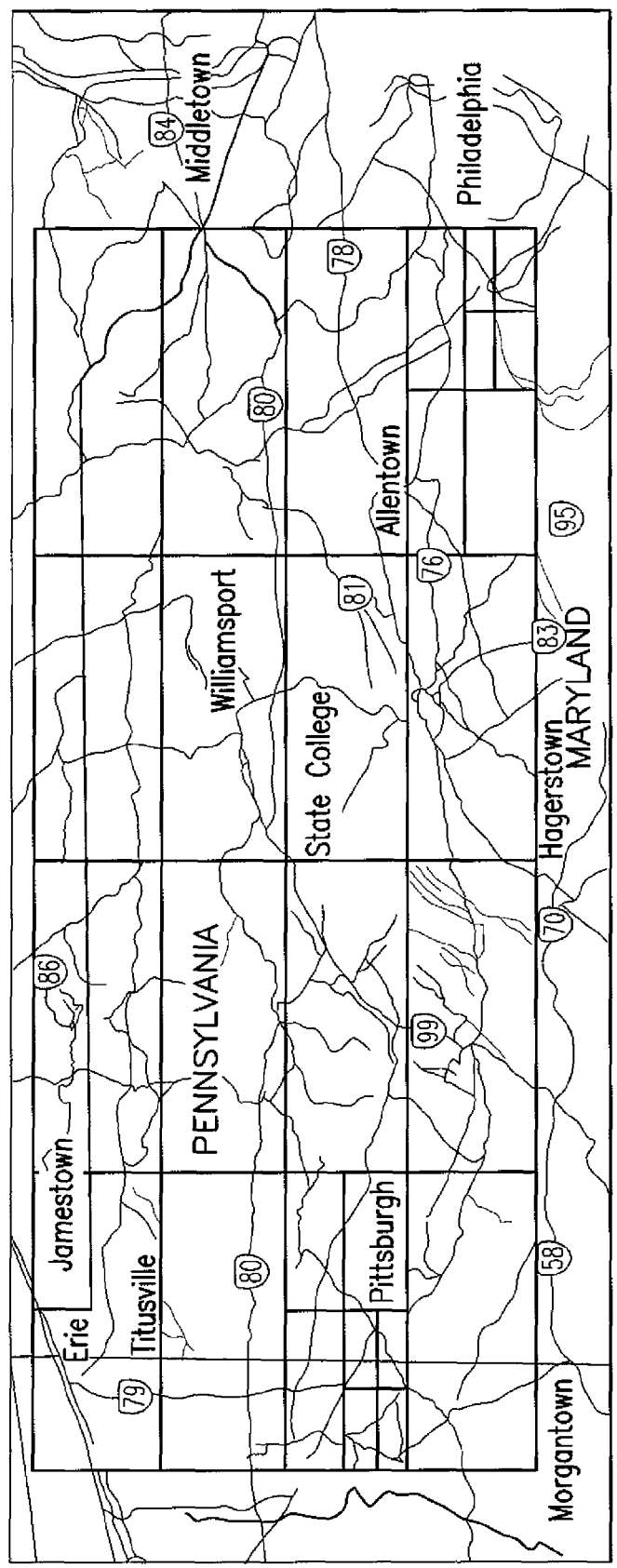
FIG. 7 illustrates an example break down of the state of Pennsylvania according to techniques of the described subject matter.

FIG. 7 illustrates a sample break down for the state of Pennsylvania for a specific instance of the N-Tree, a QuadTree, where each branch can be broken into four (4) branches, all rectangular.

The rural areas of Pennsylvania may be broken down into larger rectangles because there are a smaller amount of individuals per square mile. The urban areas of Philadelphia and Pittsburgh may be broken down into smaller rectangles (most likely smaller than shown in this simplified map) to minimize the size of the rectangle to ensure professional de-identification.

Personally identifiable data of individuals within the broken down region remains private because the population of a region, not the individuals within the region, is identified when the data is used. For example, rather than associating prescribing behaviors to individual physicians, the prescribing behavior of all physicians within a region may be used in data analysis or market sizing activities. In some embodiments, an identifier is associated with a broken down region, and the personally non-identifiable data for individuals is associated with the identifier.

An example breakdown is described to illustrate some techniques of the present subject matter. It should be understood that latitude and longitude provide a convenient way of specifying the geospatial location of individuals as well as region boundaries, such as states or bricks. In the following illustration, a Cartesian coordinate framework is used for convenience.

Figure 1:
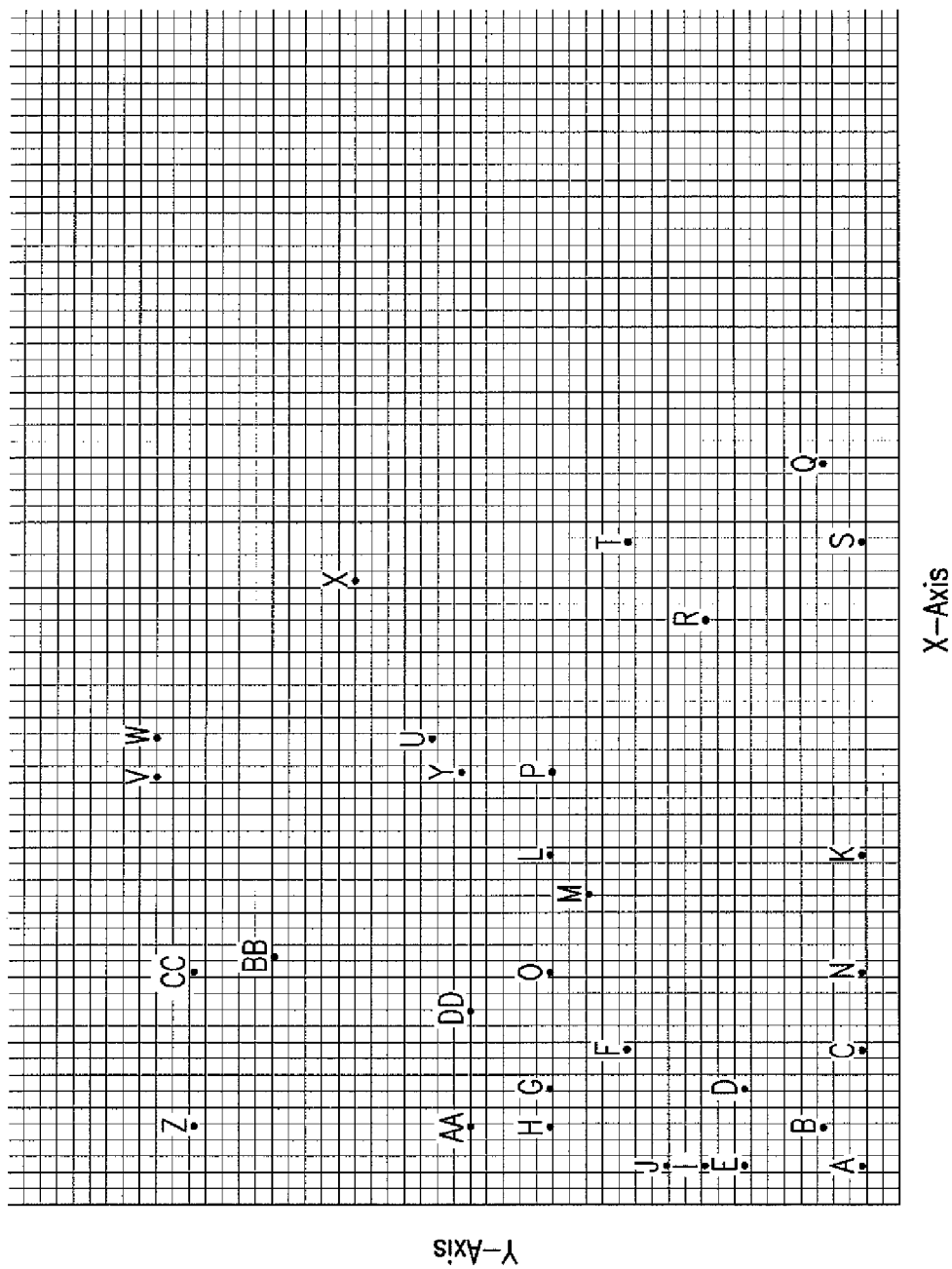
FIG. 1 illustrates an example distribution of individuals within a region according to embodiments of the described subject matter.

FIG. 1 illustrates an exemplary region 100 with individuals A-DDD located throughout the region 100. For convenience, the region is a rectangle. However, the region may be of any arbitrary shape, such as the state boundaries of one of the fifty United States (FIG. 6). For the purposes of the illustration, each dot a-dd represents the location where an individual physician practices, and the coordinates of the practice is the geospatial location of the practice.

Figure 5:
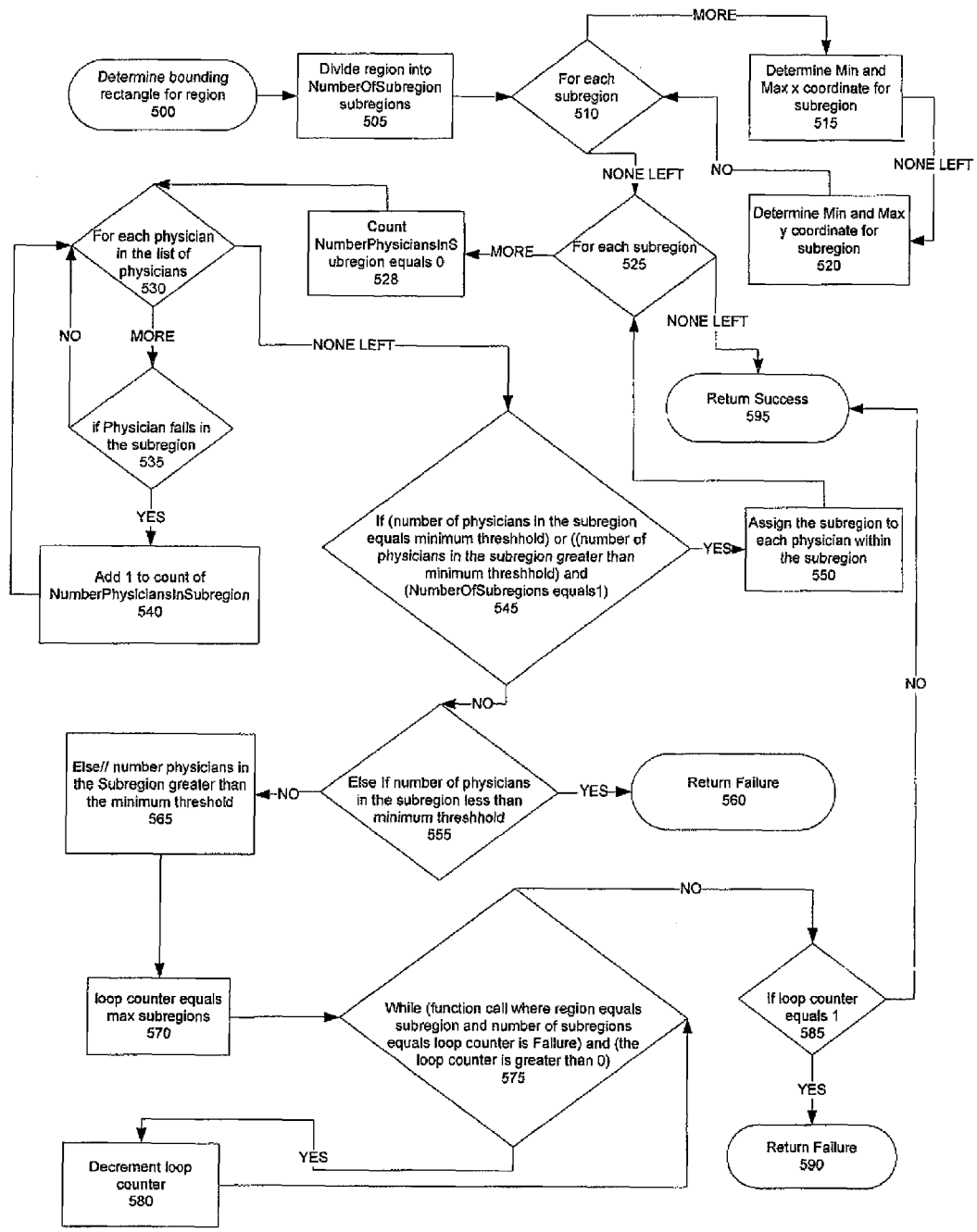
FIG. 5 illustrates an example procedure according to embodiments of the described subject matter.

FIG. 5 is a flowchart for an exemplary procedure illustrating some techniques of the described subject matter. The procedure of FIG. 5 operates with regions being broken down into at most four subregions at each level of the tree. Furthermore, the minimum number of individuals permitted in a given subregion is selected at five. However, it should be noted that in practice the described techniques are not limited to a particular number of break downs for region or a minimum threshold of individuals within the smallest subregion.

For a first level function call, in block 500, a bounding rectangle for the region is determined. Referring to FIG. 1, the bounding rectangle for the region 100 matches the boundary of the region 100 because region 100 is a rectangle. In practice, for any arbitrary shape, such as the state of Pennsylvania, a bounding rectangle may be determined. For example, if the region is the state of Pennsylvania, then the upper left coordinate of the bounding rectangle has coordinates where the x coordinate is the minimum x coordinate of any point within the state and the y coordinate is the maximum y coordinate for any point within the state. The upper right point has an x coordinate that is the maximum x coordinate for any point within the state and a y coordinate that is the maximum y coordinate for any point within the state. The lower right point of the bounding rectangle has an x coordinate that is the maximum x coordinate value for any point in the state, and a y coordinate that is the maximum y coordinate value for any point in the state. The lower left point of the bounding rectangle is the point that has both the minimum x and y coordinate values for any point in the state. The initial break down is performed based on the bounding rectangle. In other embodiments, the bounding polygon may be another shape, such as a triangle, hexagon, trapezoid, or other appropriate polygon.

Figure 2:
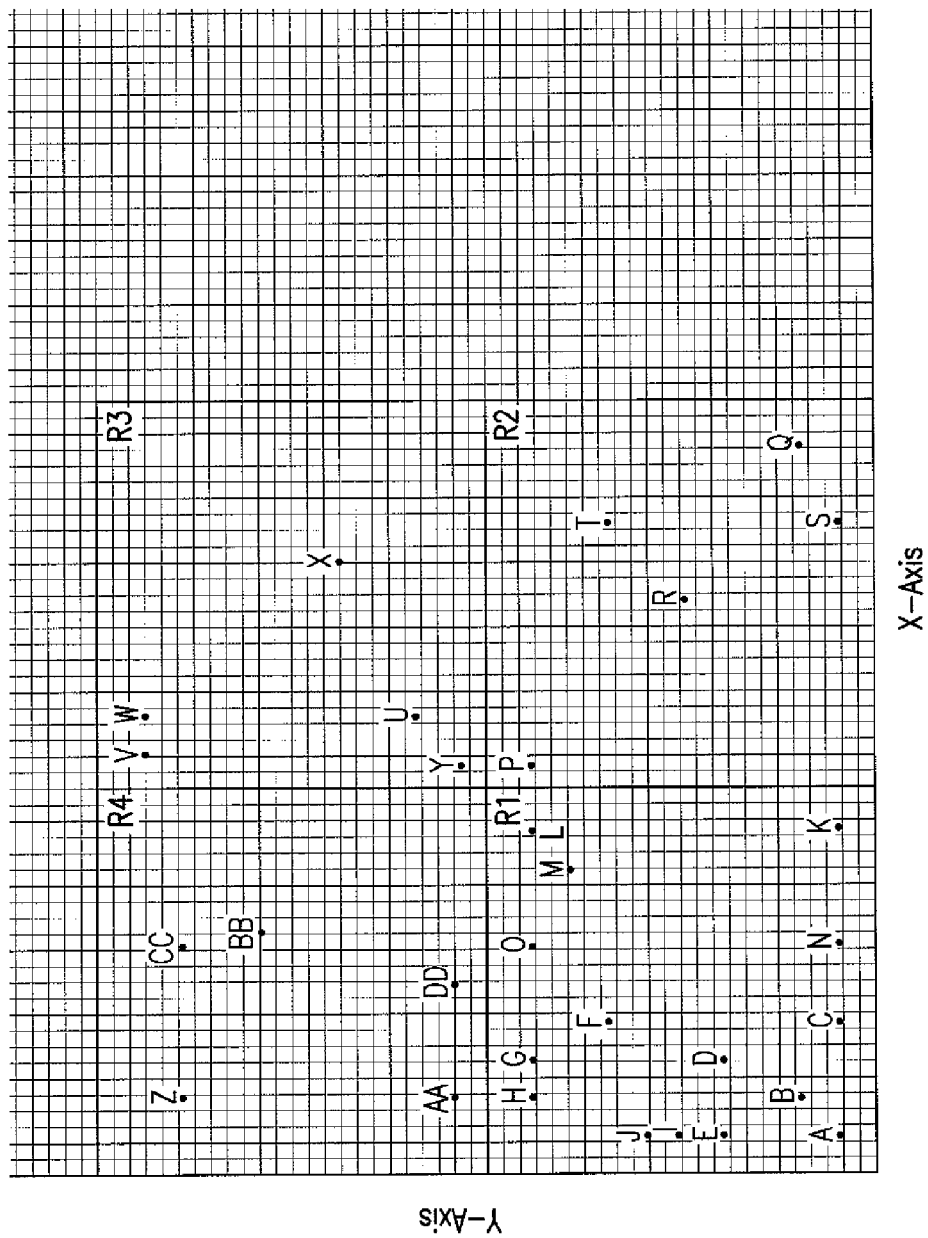
FIGS. 2-4 illustrate example break down of the region of FIG. 1 into subregions according to techniques of the described subject matter.

In block 505, the bounding rectangle is broken down into the maximum number of subregions allowed for a region. As mentioned above, this number is 4. FIG. 2 illustrates region 100 broken into four subregions R1-R4. Similar to the bounding rectangle of block 500, each of the four subregions R1-R4 is itself a rectangle. In some embodiments, the subregion break down at a given level of the procedure may be of a different shape than that of the parent level. For example, the first break down in block 505 may be triangles while break down at lower levels of the procedure may be hexagons.

Turning to FIG. 1, region R4 contains physicians Z, AA, BB, CC, and DD. Region R3 contains physicians U-Y. Region R2 contains physicians P-T. Region R1 contains physicians A-O.

Returning to FIG. 5, the boundary points for the subregions are calculated (blocks 510-520). The subregions in this embodiment are rectangles. Therefore, the lines joining the top left, top right, bottom right, and bottom left coordinates of the subregion specify the boundaries of the subregion. In some embodiments, the subregions may be of other shapes, such as right triangles. In this case, the lines joining the three vertices of the right triangle denote the subregion's boundaries. In other cases, equations denoting curves may specify all or portions of the subregion's boundaries.

Designation of the subregion's boundaries may be accomplished algorithmically, such as if the subregions are of regular shapes (squares, rectangles, triangles, etc.). For example, if a region is a square and the subregions are four equal sized squares, then the coordinates of the subregion boundary vertices may be calculated using simple equations. Assuming the four corners of the region are $(x_1,y_1)$ (lower left), $(x_2,y_1)$ (lower right), $(x_2,y_2)$ (upper right), and $(x_1,y_2)$ (upper left), then the coordinates of the lower left subregion are $(x_1,y_1)$ (upper left), $((x_2-x_1)/2,y_1)$ (lower right), $((x_2-x_1)/2, (y_2-y_1)/2)$ (upper right), and $(x_1, (y_2-y_1)/2)$ (upper left). For a region of 100 by 100, with (0,0) in the lower left corner, the coordinates of the lower left square would be (0,0), (50,0), (50,50), and (0,50). In other embodiments, the boundaries may be determined with human intervention and input into the procedure.

The coordinate framework for the illustration in FIG. 1 spans (0,0) in the lower left corner to (100,100) in the upper right corner. A subregion is selected in block 510, for example, R1. The maximum and minimum x and y coordinates are determined (blocks 515 and 520). The coordinates for the vertices of region R1 are (0,0), (50,0), (50,50), and (0,50). The procedure returns to block 510 for each subregion. When no further subregions exist, the procedure proceeds to block 525.

For each subregion (block 525), the number of physicians in the subregion is determined (blocks 530-540), and the need for further break down is determined (blocks 545-585). To determine the number of physicians in the region, a master physician list may be used. An example physician list in connection with FIG. 1 is shown in Table I below.

TABLE 1

| Physician Coordinates | |
|---|---|
| Physician | Location (in Cartesian coordinates) |
| A | 5, 5 |
| B | 10, 10 |
| C | 20, 5 |
| D | 15, 20 |
| E | 5, 20 |
| F | 20, 35 |
| G | 15, 45 |
| H | 10, 45 |
| I | 5, 25 |
| J | 5, 30 |
| K | 45, 5 |
| L | 45, 45 |
| M | 40, 40 |
| N | 30, 5 |
| O | 30, 45 |
| P | 55, 45 |
| Q | 95, 10 |
| R | 75, 25 |
| S | 85, 5 |
| T | 85, 35 |
| U | 60, 60 |
| V | 55, 95 |
| W | 60, 95 |
| X | 80, 70 |
| Y | 55, 55 |
| Z | 10, 90 |
| AA | 10, 55 |
| BB | 40, 80 |
| CC | 30, 90 |
| DD | 25, 55 |

For each physician in the list (block 530), the physician's location is determined. A counter for the number of physicians in the subregion is set to zero (block 532). Physician A's location is listed as (5,5). Assuming that the current subregion in question is R1, physician A falls into region R1 because location (5,5) is within the boundaries listed above for R1 (block 535). One is then added to the count of physicians in the subregion (block 540). Otherwise, the procedure returns to block 530 to obtain another physician. After all physicians have been considered in region R1, fifteen physicians (A-O) fall in region R1. Regions R2, R3, and R4 contain five physicians each.

In block 545, if either the number of physicians in the subregion equals the minimum threshold or the number of physicians in the subregion is greater than the threshold and the number of subregions is 1, then the current region is a lowest level region. In the first instance, if the subregion has the minimum number of physicians, the subregion cannot be broken down further and still satisfy the constraint that the number of physicians must be equal to or above the minimum threshold. Therefore, the subregion is the smallest subregion possible. In the other instance, there may be greater than the number of allowed physicians in the subregion, however, the subregion break down as a result of the higher level segmentation of the parent region does not permit further breakdown (NumberSubRegions=1). Therefore, this subregion is the smallest possible subregion. In other embodiments, if this case is encountered, the parent level breakdown may be rerun. For example, a different number of subregions, different shapes of subregions, etc., may serve as the basis of a rerun of the breakdown.

The doctors within the subregion are assigned to the subregion (block 550) and control is returned to block 530 to check the next subregion. Turning to FIG. 1, subregions R2-R4 include the minimum number of physicians allowed. Therefore, physicians P-T are assigned to R2, U-Y to R3, and Z-DD to R4.

However, for region R1, neither does R1 include the minimum number of physicians allowed for a region (R1 has 15 while the minimum is 5) nor is the number of subregions equal to 1 (because the current iteration of the procedure was called using the maximum number of subregions as the number of subregions (e.g., 4)). Returning to FIG. 5, the number of physicians (15) is not less than the minimum threshold (5) (block 555). Therefore, the subregion can be broken down further. A loop counter is set to the maximum number of subregions that the current iteration of the function was called with (in this case 4) (block 570). In block 575, the function is called with 4 as the number of subregions and the current subregion as the region to be broken down. The function call is repeated for number of subregions decremented (block 580) until the number of subregions is 1 and while the return value of function call is Failure (block 575). Returning failure indicates that the subregion break down was too granular to satisfy the constraint, here that the number of doctors in the break down (and in the subsequent recursive break downs) was greater than or equal to a minimum threshold for all subregions and recursive subregions.

Figure 3:
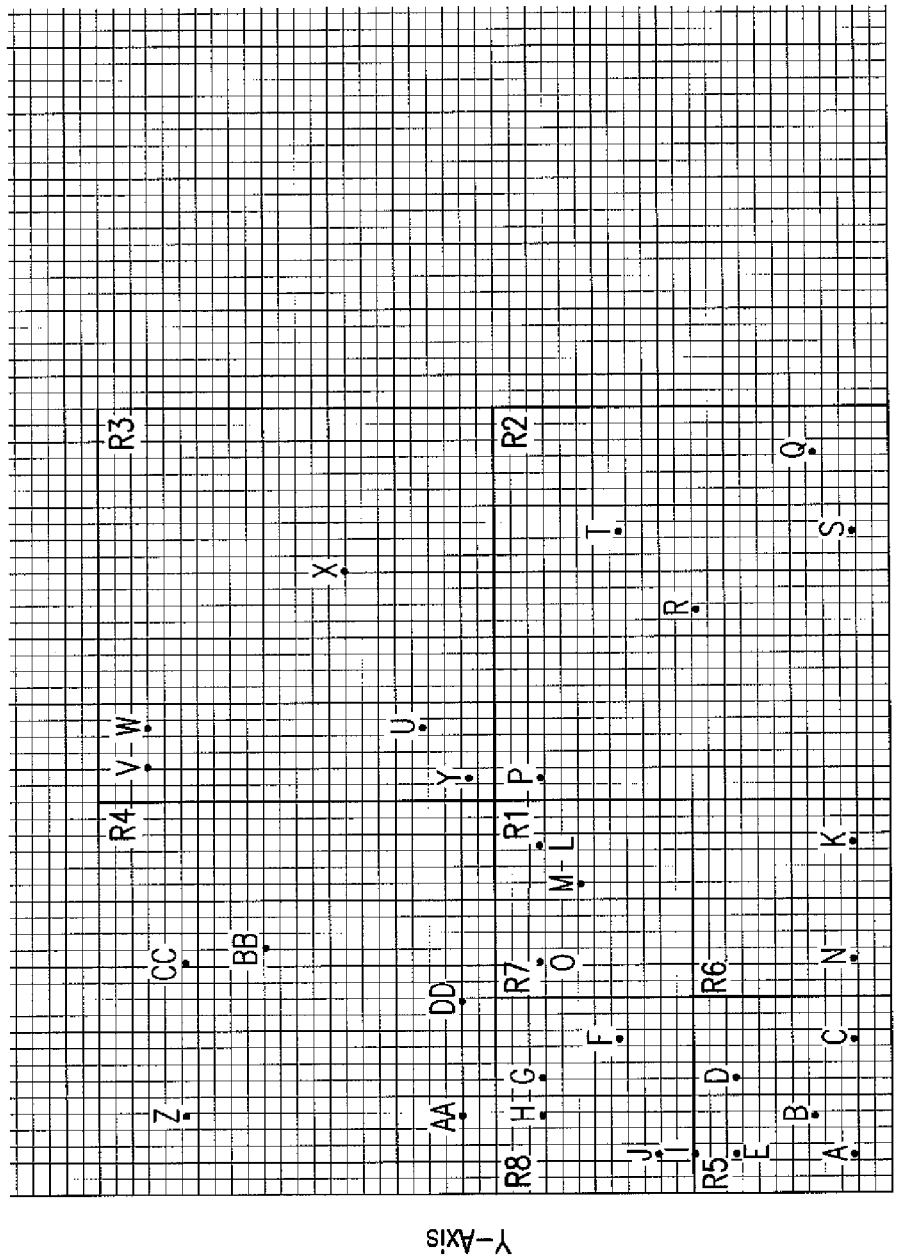

For the second level function call where the region is R1 and the number of subregions is 4, breakdown of R1 into four subregions as indicated in FIG. 3 is performed—R8, with coordinates (0,50), (25,50), (25,25), and (0,25); R7 with coordinates (25,50), (50,50), (50,25), and (25,25); R6 with coordinates (25,25), (50,25), (50,0), and 25,0); and R8 with coordinates (0,25), (25,25), (25,0), and (0,0) (blocks 500-520). As indicated in FIG. 3, R8 contains physicians F-J, R7 contains physicians L, M, and O, R6 contains physicians K and N, and R5 contains physicians A-E (blocks 525-540).

Subregions R8 and R5 contain the minimum number of physicians (block 545), however, subregions R6 and R7 contain less than the minimum number, two and three physicians, respectively (block 555). Therefore, the current second level iteration of the procedure returns Failure (block 560).

Returning to the first level iteration where the Region is the entire block of R1-R4, and the subregions are R1-R4, the loop counter is decremented to 3 (block 580), and the function is called again with region as R4 and the number of subregions is 3 (block 575).

Figure 4:
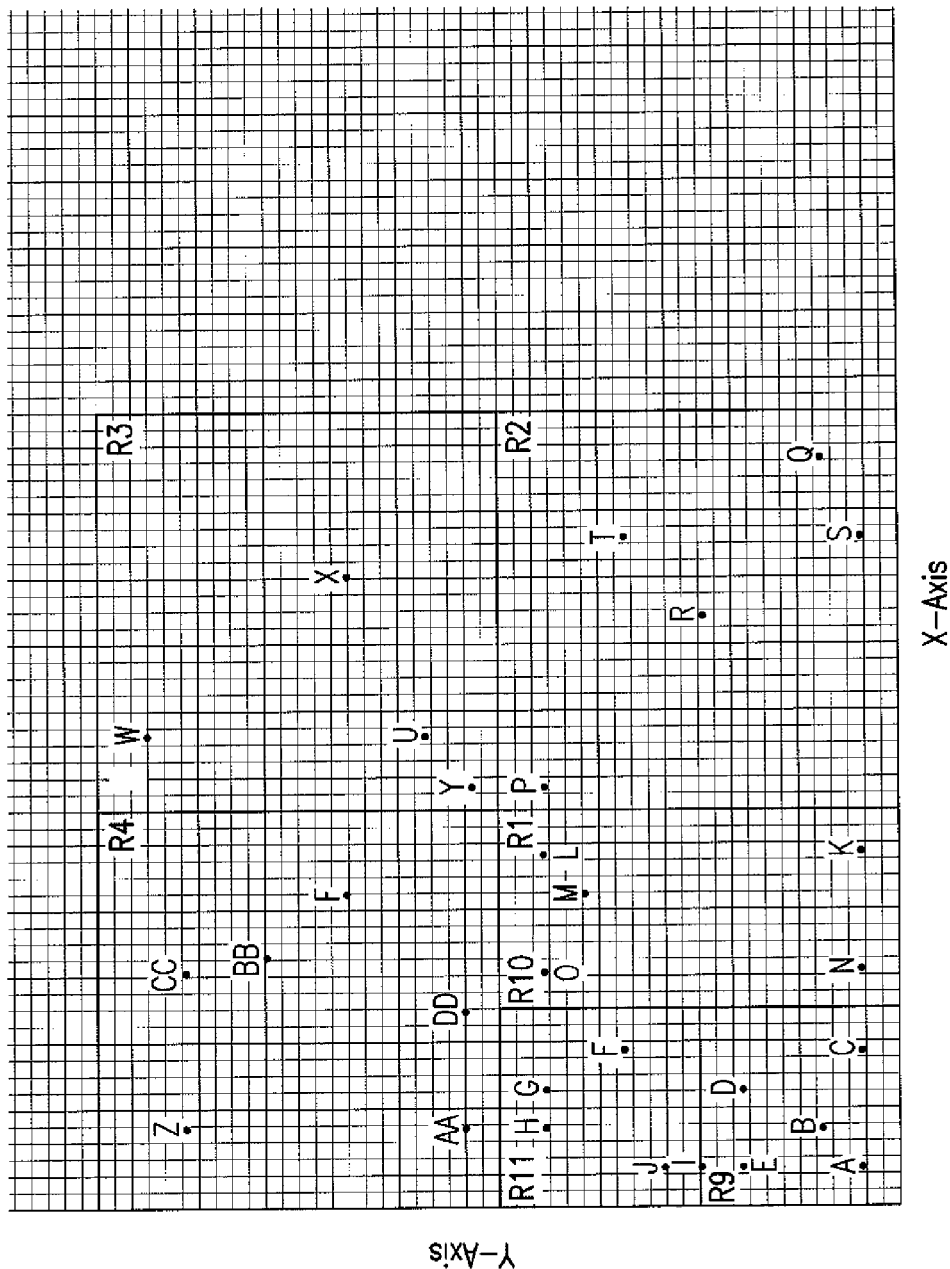

FIG. 4 depicts an exemplary break down for this function call. Region R11 has the same coordinates as R8 from the previous iteration (0,50), (25,50), (25,25), and (0,25); R9 has the same coordinates as R5 (0,25), (25,25), (25,0), and (0,0). R10 is the combination of regions R7 and R6 with the coordinates ((25,50), (50,50), (50,0), and (25,0) (blocks 500-520). R9 contains physicians A-E, R10 contains F-J, and R11 contains K-O) (blocks 525-540). Regions R9-R11 contain the minimum number of physicians, 5 (block 545). The physicians are assigned to the respective regions R9-R11 (block 550). Since each subregion satisfies the constraint (the number of physicians equals the minimum threshold), the second level function returns success (block 595).

It should be noted that if after function calls for all number of subregions until number of subregions equals 1 return failure, then the respective iteration of the function returns Failure (blocks 585-590). This may occur, for example, where a subregion that is undergoing attempted break down contains less than the minimum number of physicians. If R4 contained only two physicians, then the successive break down of R4 into four, three, two, and 1 subregion would fail, and block 590 would return Failure.

Table II below shows the region locations for the physicians in the current example embodiment.

TABLE 2

Physician Regions

| Physician | Location (in Cartesian coordinates) | Region |
|---|---|---|
| A | 5, 5 | R11 |
| B | 10, 10 | R11 |
| C | 20, 5 | R11 |
| D | 15, 20 | R11 |
| E | 5, 20 | R11 |
| F | 20, 35 | R10 |
| G | 15, 45 | R10 |
| H | 10, 45 | R10 |
| I | 5, 25 | R10 |
| J | 5, 30 | R10 |
| K | 45, 5 | R9 |
| L | 45, 45 | R9 |
| M | 40, 40 | R9 |
| N | 30, 5 | R9 |
| O | 30, 45 | R9 |
| P | 55, 45 | R4 |
| Q | 95, 10 | R4 |
| R | 75, 25 | R4 |
| S | 85, 5 | R4 |
| T | 85, 35 | R4 |
| U | 60, 60 | R3 |
| V | 55, 95 | R3 |
| W | 60, 95 | R3 |
| X | 80, 70 | R3 |
| Y | 55, 55 | R3 |
| Z | 10, 90 | R2 |
| AA | 10, 55 | R2 |
| BB | 40, 80 | R2 |
| CC | 30, 90 | R2 |
| DD | 25, 55 | R2 |

In some embodiments, break down of regions may be done into other than four subregions, such as 2, 3, 5, etc. In some embodiments, different numbers of subregion break down may be used throughout the procedure. For example, the first level break down may be done into four subregions while all second level break downs may be done into eight subregions or any appropriate number of subregions. In other embodiments, break downs at a given level may be done into different numbers of subregions. For example, with respect to FIG. 2, assuming that the number of physicians permits, R4 may be broken down into six subregions, R3 into 2, etc.

In some embodiments, the shape of subregions may be other than squares or rectangles, such as hexagons, triangles, or a combination of shapes, such as triangles and pentagons. Well known algorithms may be employed to determine the boundaries of the subregions and to determine whether the location of a particular physician falls into a subregion. Other shapes include shapes with curves, such as circles, semi-circles, etc.

In other embodiments, the minimum threshold number of physicians for a given subregion may be any appropriate number. For example, regulations may determine that sensitive data should be used in a manner that does not divulge the sensitive information of the individuals. One technique is to use aggregated data where the number of individuals in the aggregated group is above a minimum threshold (e.g., 10).

In some embodiments, individuals may be located using techniques other than Cartesian coordinates. For example, other location techniques include GPS coordinates, latitude/longitude (including degrees, minutes, and seconds), or any other geospatial location techniques.

An exemplary implementation of techniques of the described subject matter is specified below. The procedure is a top-down N-tree break down procedure for a group of professionals in a given geographic area, with certain restrictions on the minimum number of professionals in each branch of the tree.

UP-FRONT DEFINITIONS

A polygon may be associated with the following data:

- Polygon-ID ... Unique identifier for each polygon / geographic area
- Leaf-or-Branch ... Leaf is at the end of the tree, Branch has more branches or leaves
- Bounding-Rectangle ...the min bounding rectangle for this rectangle, to help with searches
- Min-Long: minimum longitude for the polygon
- Min-Lat: minimum latitude for the polygon
- Max-Long: maximum longitude for the polygon
- Max-Lat: maximum latitude for the polygon
- Parent-Branch ...the pointer to the polygon for the parent for this branch of leaf
- Number-of-Branches ...the number of branches or leaves underneath. Populated for branches.
- Branch-Polygon[Number-of-Branches] ...a pointer to the polygon for each branch / leaf. Populated for branches.
- Number-of-Points ... the number of points in the polygon defining this region. Populated for leaves.
- Points [Number-of-Points] ...each point is a Lat/Long duple. Populated for leaves.
<Professionals> ...list of professionals used for assigning to regions. These professionals need, at a minimum, a Lat/Long for their location
<Region> ... the original max size region (defined as a polygon)
- Polygon-ID ... the Polygon ID for the original region gets assigned before the initial call to N-Tree
- Bounding-Rectangle ... the bounding rectangle of the original region
- Number-of-Points ... the number of points that define this top-level region.
- Points[Number-of-Points] ...the points that define the polygon of this top-level region.

-continued

<Professional-Count> ... the minimum number of professionals in a given group to assure de-identification
<Business-Rules> ... additional rules for determining whether professionals can be grouped.
<Number-of-Leaves> ...the maximum number of leaves that will be generated for each branch.
Top-Down N-Tree Algorithm
Top-Down-N-Tree (<Region>, <List-of-Professionals>,<Number-of-Leaves>)
<Region> is the polygon to be split further (if possible)
<List-of-Professionals> are the professionals that fit into this region
Split <Region> into the number of sub-regions, as specified. Each of these sub-regions is part of <Temp-Polygon> and together these sub-regions cover the full <Region>
- For n=1 to <Number-of-Leaves>
  o <Temp-Polygon>[n].Number-of-Points = the number of points used to define this sub-region
  o For m=1 to <Number-of-Points>
    ▫ <Temp-Polygon>[n].Points[m].Lat = Latitude of the m-th point.
    ▫ <Temp-Polygon>[n].Points[m].Long = Longitude of the m-th point.
  o End For
Calculate the bounding rectangle for this polygon.
  o <Temp-Polygon>[n].Min-Long = Minimum (all longitude points for <Temp-Polygon>[n])
  o <Temp-Polygon>[n].Min-Lat = Minimum (all latitude points for <Temp-Polygon>[n])
  o <Temp-Polygon>[n].Max-Long = Maximum (all longitude points for <Temp-Polygon>[n])
  o <Temp-Polygon>[n].Max-Lat = Maximum (all latitude points for <Temp-Polygon>[n])
- End For
For each of the sub-regions just created, assign professionals to that sub-region (each professional should be assigned to only one sub-region) and see whether the business rules for de-identifying professionals allow for the further breakdown for all of the regions.
- For n = 1 to <Number-of-Leaves>
  o For m = 1 to total number of professionals
    ▫ If the Lat/Long for the <List-Of-Professionals>[m] fits within the polygon defined for <Temp-Polygon>[n] (calculated by using a standard "Point in Polygon" algorithm) AND <List-Of-Professionals>[m] has not been assigned to a sub-region yet
    - Assign <List-Of-Professionals>[m] to <Professionals> [n]
    - Mark <List-Of-Professionals>[m] as assigned
    ▫ End If
  o End For
- End For
- For n = 1 to <Number-of-leaves>
  o (If the Count for <Professionals> [n] < <Professionals-Count>) OR (<Business-Rules> applied prevent the grouping)
If one of the sub-regions doesn't meet the criteria, the split with the number of leaves will not work. Try with one less leaf and see whether it works.
    ▫ If (Number-of-Leaves > 2)
    - Call Top-Down-N-Tree(<Region>,<List-of-Professionals>,<Number-of-Leaves>−1)
    - Return (Complete)
    ▫ Else
If the number of leaves is already at 2, we have tried to break down into the smallest number of leaves, so this region cannot be broken down any further. This region is a LEAF.
    - For each of the professionals in <List-Of-Professionals>, assign ID for the <Region>.Polygon-ID.
    - <Region>.Leaf-or-Branch = LEAF
    - Return (Complete)
    ▫ End If
  o End If
- End For
If we got this far, then the sub-regions are acceptable as either leaves or branches and the Region is a branch. Mark the Region as a branch and try to move further down the list by recursively calling N-Tree.
- <Region>.Leaf-or-Branch = BRANCH
- <Region>.Number-of-Branches = <Number-of-Leaves>
- For n = 1 to Number-of-Leaves
  o <Region>.Branch-Polygon[n] = <Temp-Polygon>[n]
  o <Temp-Polygon>[n].Parent-Branch = <Region>
  o Call Top-Down-N-Tree(<Temp-Polygon>[n]>, <Professionals>[n])
- End For
- Return (Complete)
End (N-Tree)

For illustrative purposes, the procedure will be described with a simplified example. Constraints indicate that at least ten (10) physicians per specialty that practice within that region must be grouped and a grouping includes more than one type of physician. For simplification purposes, a QuadTree will be used, which divides each Branch into four (4) equal sized rectangles (branches/leaves), splitting the region in ½ horizontally and vertically each time a split occurs.

An algorithm for a top-down QuadTree for physicians follows:

- The original region will be defined as <State>, which will be a minimum bounding rectangle for the state/region in question.
- <Number-of-Leaves> is 4.
- For each of the rectangles, it is assumed that:
  o Point 1 is Lower Left Point (Min Long, Min Lat)
  o Point 2 is Lower Right Point (Max Long, Min Lat)
  o Point 3 is the Upper Left Point (Min Long, Max Lat)
  o Point 4 is the Upper Right Point (Max Long, Max Lat)

This is the initial call to develop this example QuadTree, where <State> is the bounding rectangle for the state in question and <Physician-List> is the full list of physicians to be categorized for the state in question.
- Call Top-Down-QuadTree (<State>,<Physician-List>,4)

Top-Down-QuadTree(<Region>, <Physician-List>, <Number-of-Leaves>)
<Region> is the rectangle to be split further (if possible)
<Physician-List> is the physicians that fit into this region
First, check to make sure Physicians fit within this rectangle
Split <Region> rectangle into 4 sub-rectangles (R-1, R-2, R-3, R-4), by splitting the region in half in each direction. Each of these sub-rectangles is part of <Temp-Rect>. Because it is split as described, these sub-rectangles will not overlap and together the sub-regions will make up the full <Region>
For each of the sub-rectangles just created, assign physicians to that sub-rectangle (each physician is assigned to one sub-rectangle) and see whether at least 10 physicians are assigned to each and that these physicians aren't all in the same Group Practice. If each sub-rectangle meets these criteria, then a further breakdown for all of the sub-rectangles can be performed.
If one of the sub-rectangles doesn't meet the criteria, then try to break down the Region into 3 parts, then 2 parts to see whether the Region can be broken down further. If not, this Region is the end/leaf of the tree. Assign the professionals to the region and don't break down the Region any further.
If all of the sub-rectangles meet the criteria, then the sub-regions are acceptable as either leaves or branches and the Region is a branch. Mark the Region as a branch and try to move further down the list by recursively calling QuadTree.
End (Top-Down-QuadTree)
N-Tree-Predefined-Polys
There will be cases where pre-defined geographic polygons will be desirable as a standard set of regions from which the tree structure can be constructed. In the case of using these pre-defined polygons, the polygons can be split (if there are too many professionals in a single polygon), or the polygons can be combined (if the number of professionals in a single polygon is not sufficient). Fore example, if the pre-defined geographic boundaries are 5-digit ZIP codes, the following can occur:
- A ZIP code can be split so that two (2) or more different sub-regions are formed from this ZIP code.
- Two (2) or more different ZIP codes can be combined so that a sub-region now includes these multiple ZIP codes.

In the example embodiments, as described above, the top-level region (e.g., the state) will be decomposed to one level below, to include all of the pre-defined geographic polygons. It is assumed that all professionals to be placed into the region will fall geographically into one of these polygons.
The N-Tree-Predefined-Polys function will work very similarly to the Top-Down-N-Tree function. The <Top-Level-Region> will be defined in the following manner:
- Polygon-ID = Top-Level-Polygon-ID
- Leaf-or-Branch = BRANCH    ... the pre-defined polygons will be leaves below this region.
- Bounding-Rectangle = minimum bounding rectangle of the top-level region
- Parent-Branch = NULL
- Number-of-Branches = the number of pre-defined polygons
- Branch-Polygon[n] = the pointer to each of the pre-defined polygons below the top-level.

Each of the pre-defined polygons will be defined in the following manner:
- Polygon-ID = Polygon-ID for that polygon
- Leaf-or-Branch = LEAF    ...initially, it will be a leaf, but could be broken down into a branch later
- Bounding-Rectangle = the Min & Max Longs and Lats, found from the Points field in this polygon
- Parent-Branch = <Top-Level-Region>
- Fixed-Polygon = True ...indicates that this is one of the fixed polygons.
- Number-of-Points = the number of points used to define this polygon.
- Points[n] = all of the points used to define this polygon.

<Professionals>    ... list of professionals used for assigning to regions. These professionals need, at a minimum, a lat/long for their location
<Region>    ... the original max size region (defined as a polygon)
- Polygon-ID    ... the Polygon ID for the original region gets assigned before the initial call to N-Tree
- Bounding-Rectangle    ... the bounding rectangle of the original region

- Number-of-Points ... the number of points that define this top-level region.
- Points [Number-of-Points] ...the points that define the polygon of this top-level region.

<Professional-Count> ... the minimum number of professionals in a given group to assure de-identification
<Business-Rules> ... additional business rules for determining whether professionals can be grouped.
<Number-of-Leaves> ...the maximum number of leaves that will be generated for each branch.
N-Tree-Predefined-Polys Algorithm
N-Tree-Predefined-Polys (<Region>, <List-of-Professionals>,<Number-of-Leaves>)
<Region> is the polygon to be split further (if possible)
<List-of-Professionals> are the professionals that fit into this region
First, assign all professionals to one of the pre-defined polygons immediately below the top-level region.
Go through each of these pre-defined polygons and mark each one on whether it is an acceptable polygon or not. "Acceptable" means that the number of professionals is GE <Professionals-Count> and <Business-Rules> do not prevent the grouping.
If all of the pre-defined polygons are acceptable, then they can be broken down by the standard Top-Down-N-Tree algorithm. And the defining of polygons is complete.
- For m = 1 to <Number-of-Predefined-Polygons>
  ○ Call Top-Down-N-Tree(<Region>.Branch-Polygon[n], <List-of-Professionals>,<Number-of-Leaves>)
- End For
- Return If one or more of the pre-defined polygons are not acceptable, each of the unacceptable ones needs to be merged with one or more other pre-defined polygons until all unacceptable polygons have been merged. The basic process for merging these polygons is:
- BEGINNING
- Sort the pre-defined polygons and newly merged polygons by (1) whether they are acceptable and (2) by the number of professionals in the polygon (<Initial-Polygon>)
- Start with the polygon that is unacceptable AND has the lowest number of professionals.
- Find all of this polygon's neighbors.
- Sort the neighbor list by (1) whether they are acceptable and (2) by the number of professionals in the neighbor.
- Begin merging <Initial-Polygon> with its neighbors in sorted order until all the merged polygon is Acceptable.
○ Once Acceptable:
  □ Create the new Merged-Polygon so that the Top-Level-Region now points to the newly merged polygon and the newly merged polygon points to each of the individual polygons used to create the newly merged polygon.
  □ Assign the newly merged polygon a new Polygon-ID
  □ Assign all of the professionals that fit within this merged polygon to the new Polygon-ID
  □ Do not try to break down this newly merged polygon any further
  □ Cycle back up to BEGINNING to try to merge any remaining polygons.
Once complete with merging the pre-defined polygons where necessary, there should be no more unacceptable polygons.
For any pre-defined polygons that were not merged, but are acceptable, Call Top-Down-N-Tree for these polygons to break them down into smaller polygons.

Other embodiments include techniques for updating the N-Tree break down with Changes in the Professional List. It is anticipated that, periodically, revisions to the N-Tree polygons will be made to account for movement in professionals. If enough professionals move out of a polygon, the resulting professionals in the polygon may violate the rules for the polygon, necessitating re-calculations of the polygons. In addition, if professionals move into a polygon, re-calculation of the polygons may be made to better optimize the number of professionals in each polygon.

The described techniques may leave a "buffer" on the minimum number of professionals for a polygon to allow for typical movement of professionals during a year. Changes in polygons may occur annually.

In some embodiments, the N-Tree revisions may re-calculate polygon locations for all professionals in all regions. In other embodiments, re-calculation may be performed for just the polygons that have reached the threshold, either minimum or maximum.

In some embodiments, break down of regions into the smallest possible regions includes the smallest region for given parameters of the break down procedure or techniques of the break down procedure. For example, an optimal break down procedure for a given region may use triangles at a first break down level, hexagons at a second, and squares at a third. However, for ease of implementation/understanding, the break down procedure may be run with square subregions. The smallest square subregions may be considered the smallest regions despite an implementation of the break down procedure that may yield a smaller break down region.

In another embodiment, the following procedure illustrates revising the N-Tree polygons given changes to location(s) for one (1) or more professionals.

For this exemplary procedure, the following terms apply:

<Professionals> ... list of professionals used for assigning to regions. These professionals need, at a minimum, a lat/long for their location
<Number-of-Changed-Professionals> ... the number of professionals that changed locations.

```
<Changed-Professionals-Index>   ...pointer into the <Professionals> list for who changed
locations.
<Region>                 ... the original max size region (defined as a polygon)
<Professional-Count>     ... the minimum number of professionals in a given group to assure de-
identification
<Business-Rules>         ... additional business rules for determining whether professionals can be
grouped.
<Number-of-Leaves>       ...the number of leaves that will be generated for each branch.
<Max_Threshold>          ...the maximum number of professionals in a given group before re-
calculation should occur for that polygon.
N-Tree Revisions Algorithm
N-Tree-Revisions (<Region>, <List-of-Professionals>, <Changed-Professionals>)
Assign each professional to their new polygons based on the current tree structure of the
polygons.
• For m = 1 to <Number-of-Changed-Professionals>
o  <List-of-Professionals>[<Changed-Professionals-Index>[m]].Polygon-ID =
☐  Call Find-Leaf(<Region>,
       <List-of-Professionals>[<Changed-Professionals-Index>[m]].Long,
     <List-of-Professionals>[<Changed-Professionals-Index>[m]].Lat)
Traverse the tree and change the composition of leaves where necessary.
• Call Change-Leaves (<Region>,<List-of-Professionals>)
End (N-Tree-Revisions)
Change-Leaves(<Region>,<List-of-Professionals>)
First, check to see whether the branch we are on in the tree has branches or leaves below it.
If it has branches, move on to the next level.
• If (<Region>.Branch-Polygon[1].Leaf-or-Branch = BRANCH)
o  For (m = 1 to <Region>.Number_Branches)
☐  Call Change-Leaves(<Region>.Branch-Polygon[m],<List-of-Professionals>)
o  End For
• Else
If there are leaves below it, look through each one of the leaves to see whether there are an
acceptable number of professionals in these leaves.
o  Acceptable-Leaves = TRUE
o  Number-of-Leaves-Too-Large = 0
o  For (m = 1 to <Region>.Number-of-Branches)
☐  <Leaf> = <Region>.Branch-Polygon[m]
☐  Leaf-ID = <Leaf>.Polygon-ID
☐  <Leaf-Professionals> = subset of <List-of-Professionals> that fall within this leaf
☐  If (the Count of Professionals within <Leaf-Professionals> < Professional-Count) OR
(<Business-Rules> applied prevent the grouping of <Leaf-Professionals>)
•  Acceptable-Leaves = SOME-LEAVES-TOO-SMALL
•  Break out of For Loop
☐  Else If (the Count of Professionals within <Leaf-Professionals> > Max_Threshold)
•  Acceptable-Leaves = SOME-LEAVES-TOO-LARGE
•  Increment Number-of-Leaves-Too-Large by 1
•  Leaves-Too-Large[Number-of-Leaves-Too-Large] = m
☐  End If
o  End For
If there are an acceptable number of professionals in each leaf, do nothing and move on.
o  If (Acceptable-Leaves = TRUE)
☐  Return
o  Else if (Acceptable-Leaves = SOME-LEAVES-TOO-LARGE
If none of the leaves have too few and one or more of the leaves has too many, try to break out
those leaves into smaller leaves.
☐  For (m = 1 to Number-of-Leaves-Too-Large)
•  <Leaf> = <Region>.Branch-Polygon[Leaves-Too-Large[m]]
•  Call N-Tree(<Leaf>, <List-of-Professionals>,<Number-of-Leaves>)
☐  End For
If any of the leaves have too few professionals, roll up the branch and try to break out the branch
o  Else
☐  Need-To-Roll-Up = TRUE
☐  <New-Region> = <Region>.Parent-Branch
☐  Do While (Need-To-Roll-Up)
•  <New-Region-Professionals> = subset of <List-of-Professionals> that fall within this
<New-Region>
•  If (the Count of Professionals within <New-Region-Professionals> .GE. Professional-
Count) AND
(<Business-Rules> applied do not prevent the grouping of <New-Region-Professionals>)
If all the professionals could fit within this new branch, then don't need to try to roll up any
more. Just build the new tree and assign the professionals and it is complete.
Building the new tree will mean calling Top-Down-N-Tree if we are not at the top level of pre-
defined polygons.
o  If <New-Region>.Fixed-Polygon != TRUE
☐  Call Top-Down-N-Tree(<New-Region>, <List-of-Professionals>,<Number-of-Leaves>)
Otherwise, we have pre-defined polygons, so need to break out by the pre-defined polygon
algorithm.
o  Else
☐  Call N-Tree-Predefined-Polys(<New-Region>, <List-of-Professionals>,<Number-of-
Leaves>)
```

-continued

```
o    Need-To-Roll-Up = FALSE
•    Else
If the current branch (even after being rolled up) does not meet the minimum criteria, we need to
continue to roll up to higher levels of the tree until we meet the minimum criteria.
o    <New-Region> = <Region>.Parent-Region
o    If (<New-Region> = NULL)
If we're at the top and have not met the criteria, then stop.
☐    Need-To-Roll-Up = FALSE
o    End If
•    End If
☐    End Do While
o    End If
•    End If
End (Change-Leaves)
Find-Leaf (<Region>,Long, Lat)
Finds the leaf within which the Lat/Long is located.
If the Lat / Long doesn't even fit within this Region's bounding rectangle, then Return False.
•    If ((Long < <Region>.Min-Long) OR ( Long > <Region>.Max-Long))   OR
((Lat < <Region>.Min-Lat) OR ( Lat > <Region>.Max-Lat))
o    Return (FALSE)
•    End If
If the procedure has traversed down to a Leaf, then determine whether the Lat/Long fits within
that Leaf. Return the <Region> if it does or FALSE if it doesn't.
•    If (<Region>.Leaf-or-Branch = LEAF)
o    If (Long and Lat fit within the polygon defined by <Region>.Points)
☐    Return (<Region>)
o    Else
☐    Return (FALSE)
o    End If
•    Else
If the region is a Branch, continue traversing down the branch until the leaf that fits is found.
o    For m = 1 to <Region>.Number-of-Branches
☐    If ((Leaf = Call Find-Leaf(<Region>Branch-Polygon[m],Long,Lat)) !=LSE)
•    Return (<Leaf>)
☐    End If
o    End For
•    Return (FALSE)
End (Find-Leaf)
```

It will be appreciated by those skilled in the art that the techniques of the described subject matter can be implemented on various standard computer platforms operating under the control of suitable software. In some cases, dedicated computer hardware, such as a peripheral card in a conventional personal computer, can enhance the operational efficiency of the above techniques.

Figure 8:
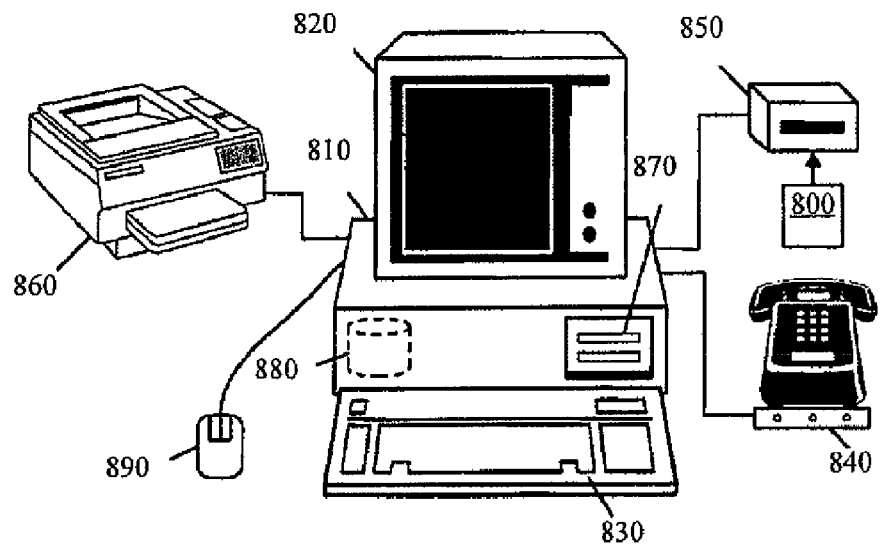
FIGS. 8 and 9 illustrate exemplary components of the described subject matter.
Figure 9:
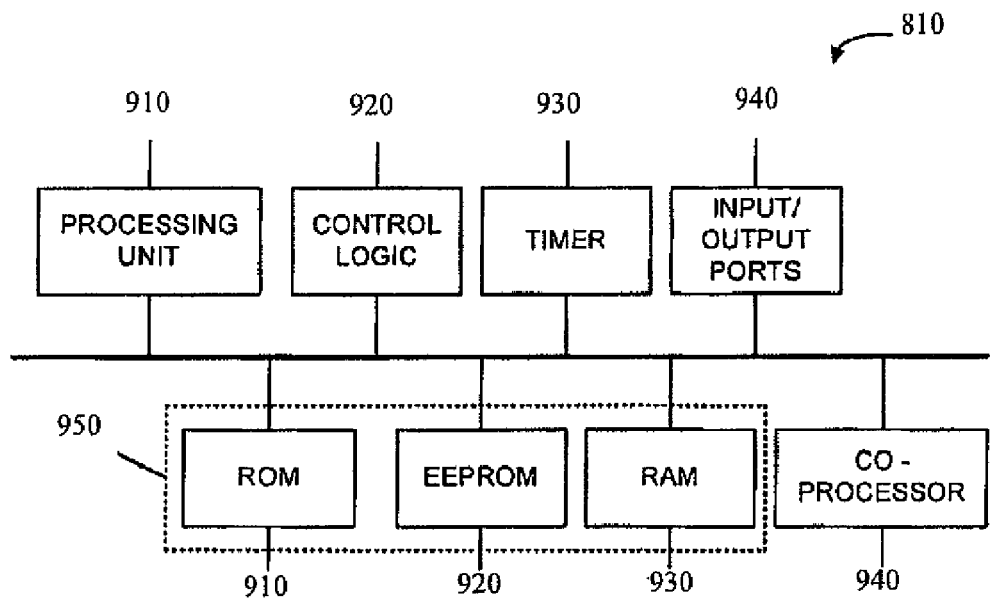

FIGS. 8 and 9 show exemplary computer hardware arrangements suitable for performing the techniques of the presently described subject matter. Referring to FIG. 8, the computer arrangement includes a processing section 910, a display 920, a keyboard 930, and a communications peripheral device 940 such as a modem. The computer arrangement may include a digital pointer 990 such as a "mouse." The computer arrangement also may include other input devices such as a card reader 950 for reading an account card 900. In addition, the computer arrangement may include output devices such as a printer 960. The computer hardware arrangement may include a hard disk drive 980 and one or more additional disk drives 970 that can read and write to computer readable media such as magnetic media (e.g., diskettes or removable hard disks), or optical media (e.g., CD-ROMS or DVDs). Disk drives 970 and 980 may be used for storing data and application software.

FIG. 10 shows an exemplary functional block diagram of processing section 910 in the computer arrangement of FIG. 9. Processing section 910 includes a processing unit 1010, a control logic 1020, and a memory unit 1050. Processing section 910 may also include a timer 1030 and input/output ports 1040. Processing section 910 may further include an optional co-processor 1060, which is suitably matched to a microprocessor deployed in processing unit 1010. Control logic 1020 provides, in conjunction with processing unit 1010, controls necessary to handle communications between memory unit 1050 and input/output ports 1040. Timer 1030 may provide a timing reference signal for processing unit 1010 and control logic 1020. Co-processor 1060 enhances the ability to perform complex computations in real time, such as those required by cryptographic algorithms. Memory unit 1050 may include different types of memory, such as volatile and non-volatile memory and read-only and programmable memory. Memory unit 1050 may, for example, include read-only memory (ROM) 1052, electrically erasable programmable read-only memory (EEPROM) 1054, and random-access memory (RAM) 1056. Various computer processors, memory configurations, data structures and the like can be used to practice the presently described subject matter, and the presently described subject matter is not limited to a specific platform.

In accordance with the presently described techniques, software (i.e., instructions) for implementing the aforementioned de-identification of healthcare data (algorithms) can be provided on computer-readable media. It will be appreciated that each of the steps (described above in accordance with these presently described techniques), and any combination of these steps, can be implemented by computer program instructions. These computer program instructions can be loaded onto a computer or other programmable apparatus to produce a machine such that the instructions, which execute on the computer or other programmable apparatus, create means for implementing the functions of the aforementioned techniques. These computer program instructions can also be stored in a computer-readable memory that can direct a computer or other programmable apparatus to function in a particular manner such that the instructions stored in the computer-readable memory produce an article of manufacture including instruction means, which implement the functions of the aforementioned demand forecasting techniques. The computer program instructions can also be loaded onto a computer or other programmable apparatus to cause a series of operational steps to be performed on the computer or other programmable apparatus to produce a computer implemented process such that the instructions which execute on the computer or other programmable apparatus provide steps for implementing the functions of the aforementioned techniques. It will also be understood that the computer-readable media on which instructions for implementing the aforementioned techniques include, without limitation, firmware, microcontrollers, microprocessors, integrated circuits, ASICS, and other available media.

It will be understood, further, that the foregoing is only illustrative of the principles of the described techniques, and that those skilled in the art can make various modifications without departing from the scope and spirit of the described techniques.

What is claimed is:

1. A method of de-identification of health care data, comprising;
determining, by one or more computers, a geographic region, wherein the geographic region has boundaries defined by a set of boundary points;
determining a location of each individual within the geographic region;
segmenting the geographic region into at least one geographic subregion, wherein each geographic subregion has boundaries defined by a set of boundary points, and wherein a number of individuals located within each geographic subregion is greater than or equal to a minimum threshold number of individuals; and
for each geographic subregion:
associating the geographic subregion with each individual located within the boundaries of the geographic subregion, and
aggregating data for each associated individual into data for the geographic subregion.

2. The method of claim 1, wherein each geographic subregion is a smallest possible subregion.

3. The method of claim 1, wherein segmenting includes performing a recursive N-Tree break down procedure.

4. The method of claim 3, further comprising:
at each level of the recursive segmentation procedure, breaking down a region into polygon shaped regions.

5. The method of claim 4, wherein the polygons are selected from the group consisting of squares, rectangles, trapezoids, rhombi, triangles, and hexagons.

6. The method of claim 4, wherein the polygons are of varying shapes.

7. The method of claim 1, further comprising:
resegmenting one or more of the geographic subregions to account for the migration of individuals from one geographic subregion to another.

8. The method of claim 1, wherein the geographic region is segmented into a maximum number of geographic subregions.

9. A system for de-identification of health care data comprising a processing arrangement, the processing arrangement including one or more processors, memory, and data storage, the processing arrangement configured to perform:
determining a geographic region, wherein the geographic region has boundaries defined by a set of boundary points;
determining a location of each individual within the geographic region;
segmenting the geographic region into at least one geographic subregion, wherein each geographic subregion has boundaries defined by a set of boundary points, and wherein a number of individuals located within each geographic subregion is greater than or equal to a minimum threshold number of individuals; and
for each geographic subregion:
associating the geographic subregion with each individual located within the boundaries of the geographic subregion, and
aggregating data for each associated individual into data for the geographic subregion.

10. The system of claim 9, wherein each geographic subregion is a smallest possible subregion.

11. The system of claim 9, wherein segmenting includes performing a recursive N-Tree break down procedure.

12. The system of claim 11, wherein the processing arrangement is further configured to perform the steps of:
at each level of the recursive segmentation procedure, breaking down a region into polygon shaped regions.

13. The system of claim 12, wherein the polygons are selected from the group consisting of squares, rectangles, trapezoids, rhombi, triangles, and hexagons.

14. The system of claim 12, wherein the polygons are of varying shapes.

15. The system of claim 9, wherein the processing arrangement is further configured to perform the steps of:
resegmenting one or more of the geographic subregions to account for the migration of individuals from one geographic subregion to another.

16. The system of claim 9, wherein the geographic region is segmented into a maximum number of geographic subregions.

17. A non-transitory computer readable medium storing software comprising instructions executable by one or more computers which, upon such execution, cause the one or more computers to perform operations comprising:
determining a geographic region, wherein the geographic region has boundaries defined by a set of boundary points;
determining a location of each individual within the geographic region;
segmenting the geographic region into at least one geographic subregion, wherein each geographic subregion has boundaries defined by a set of boundary points, and wherein a number of individuals located within each geographic subregion is greater than or equal to a minimum threshold number of individuals; and
for each geographic subregion:
associating the geographic subregion with each individual located within the boundaries of the geographic subregion, and
aggregating data for each associated individual into data for the geographic subregion.

18. The computer readable medium of claim 17, wherein each geographic subregion is a smallest possible subregion.

19. The computer readable medium of claim 17, wherein segmenting includes performing a recursive N-Tree break down procedure.

20. The computer readable medium of claim 19, further comprising:
   at each level of the recursive segmentation procedure, breaking down a region into polygon shaped regions.

21. The computer readable medium of claim 20, wherein the polygons are selected from the group consisting of squares, rectangles, trapezoids, rhombi, triangles, and hexagons.

22. The computer readable medium of claim 20, wherein the polygons are of varying shapes.

23. The computer readable medium of claim 17, further comprising:
   resegmenting one or more of the geographic subregions to account for the migration of individuals from one geographic subregion to another.

* * * * *